United States Patent
Shaw et al.

(10) Patent No.: US 7,384,953 B2
(45) Date of Patent: Jun. 10, 2008

(54) PURIFICATION OF RAPAMYCIN

(75) Inventors: Chia-Cheng Shaw, St. Laurent (CA); Warren Chew, Outremont (CA); Bogdan Kazimierz Wilk, New City, NY (US)

(73) Assignee: Wyeth, Madison, NJ (US)

( * ) Notice: Subject to any disclaimer, the term of this patent is extended or adjusted under 35 U.S.C. 154(b) by 163 days.

(21) Appl. No.: 11/359,294

(22) Filed: Feb. 22, 2006

(65) Prior Publication Data
US 2006/0199954 A1 Sep. 7, 2006

Related U.S. Application Data

(60) Provisional application No. 60/657,910, filed on Mar. 2, 2005.

(51) Int. Cl.
*C07D 498/18* (2006.01)
*A61K 31/435* (2006.01)

(52) U.S. Cl. ...................... 514/291; 540/456
(58) Field of Classification Search ............... 540/456; 514/291
See application file for complete search history.

(56) References Cited

U.S. PATENT DOCUMENTS

| 3,993,749 | A | 11/1976 | Sehgal et al. |
| 5,362,718 | A | 11/1994 | Skotnicki et al. |
| 6,277,983 | B1 | 8/2001 | Shaw et al. |
| 2001/0039338 | A1 | 11/2001 | Shaw |
| 2005/0014777 | A1 | 1/2005 | Zhu |
| 2005/0033046 | A1 | 2/2005 | Chew et al. |

FOREIGN PATENT DOCUMENTS

| WO | WO-2005/010010 A1 | 2/2005 |
| WO | WO-2005/016935 | 2/2005 |

OTHER PUBLICATIONS

Communication—International Search Report in International Application No. PCT/US2006/006212, mailed Jun. 22, 2006.

*Primary Examiner*—Bruck Kifle
(74) *Attorney, Agent, or Firm*—Arnold S. Milowsky; Howson & Howson LLP

(57) ABSTRACT

Purified rapamycin and a chemical process for obtaining the purified rapamycin are described.

20 Claims, No Drawings

PURIFICATION OF RAPAMYCIN

CROSS-REFERENCE TO RELATED APPLICATIONS

This application claims the benefit under 35 USC 119(e) of the priority of U.S. patent application Ser. No. 60/657,910, filed Mar. 2, 2005.

BACKGROUND OF THE INVENTION

This invention relates to a chemical process for the purification of rapamycin.

Rapamycin is a macrocyclic triene antibiotic produced naturally by *Streptomyces hygroscopicus*. It has been found useful in an array of applications based on its antitumoral and immunosuppressive effects. Uses include preventing or treating systemic lupus erythematosis, pulmonary inflammation, insulin dependent diabetes mellitus, smooth muscle cell proliferation and intimal thickening following vascular surgery, adult T-cell leukemia/lymphoma, and ocular inflammation. Rapamycin and rapamycin derivatives continue to be studied for treatment of these and other conditions.

Isomers of rapamycin are known which have structures below, referred to herein as Isomer B and Isomer C:

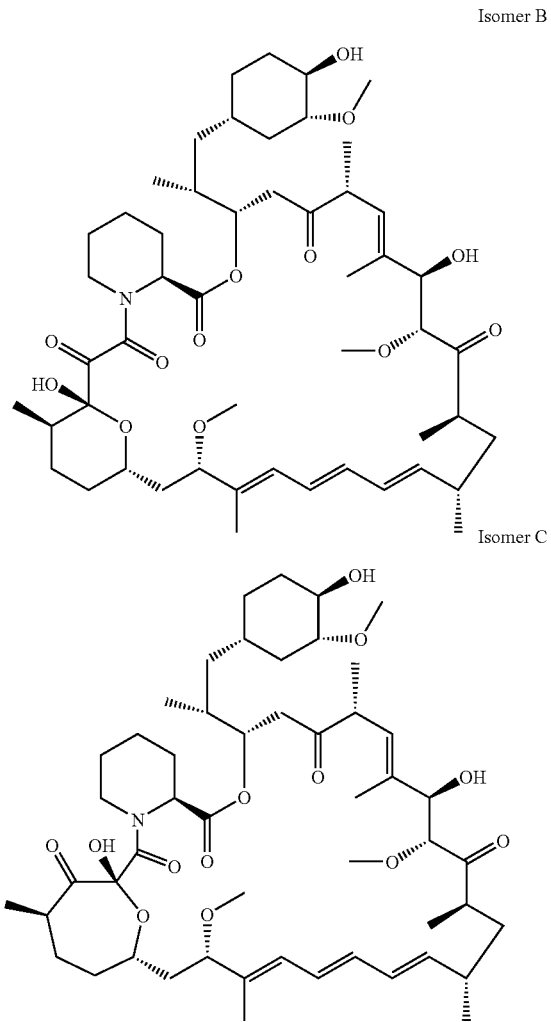

Conventional production of rapamycin is by way of fermentation. The fermentation process yields a low grade rapamycin product containing impurities, which is often colored (including troublesome yellow color), as opposed to a pure white product. Current purification methods require isopropanol recrystallization and/or charcoal treatment methods. The product obtained by these methods has a purity of approximately 94% (based on the sum of the individual purities of isomers B and C), and a yellow index of about 2. Repeated recrystallizations are often necessary to increase rapamycin purity, reduce the yellow index and increase the low B:C isomeric ratio to meet a minimum of approximately 23:1, resulting in low yields upon crystallization. As a result, production costs remain high.

What is needed is a chemical purification process to increase yield of rapamycin having sufficient purity and yield to meet quality and regulatory standards for pre-clinical and commercial use.

SUMMARY OF THE INVENTION

The invention provides a chemical process as an alternative method for the purification of rapamycin. This method is useful for crude rapamycin or second crop recovered from mother liquors during the isopropanol recrystallization. This material in general is dark brown in color with low purity and low B:C isomeric ratio. The purification process includes treatment of rapamycin with chlorotrimethylsilane to yield 31,42-bis-trimethylsilyl ether, heptane extraction, and de-protection of the 31,42-bis-trimethylsilyl ether to yield a purified rapamycin product.

In another aspect, a rapamycin generated is buffered in order to increase the ratio of B isomer to C isomer in the drug substance.

In another embodiment, purified rapamycin is precipitated, collected via filtration, washed, and then dried under vacuum in order to yield a final product.

Other aspects and advantages of the invention will be apparent from the following detailed description of the invention.

DETAILED DESCRIPTION OF THE INVENTION

The present invention provides a novel chemical process for the purification of a rapamycin.

As used herein, the terms low grade or crude are intended to mean rapamycin having a purity of less than 90%, a yellow index greater than 2, and a B:C isomeric ratio (also referred to herein as an isomeric B:C ratio) less than 20:1. In one embodiment, the B:C isomeric ratio is in the range of 13:1 to 11:1.

Scheme 1 on the following page provides an overview of the purification process. In the first step, low grade rapamycin is silylated in order to form rapamycin 31,42-bis-O-trimethylsilyl ether (also known as rapamycin 31,42-bis-O-TMS). This silylation reaction is

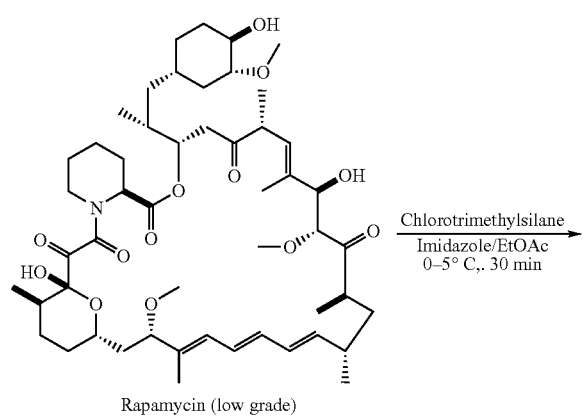

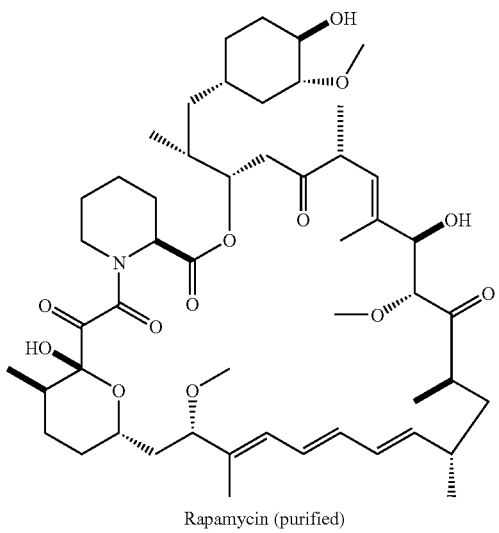

Rapamycin (purified)

described in detail in U.S. Pat. No. 6,277,983 (Shaw, et al.).

Briefly, silylation is accomplished by treating the crude rapamycin at about 0° C. to about 5° C. with chlorotrimethylsilane in an inert solvent in the presence of a suitable base. In one embodiment, the solvent is ethyl acetate (EtOAc). In another embodiment, the silylation agent is chlorotriethylsilane. In one embodiment, the base is an imidazole, such as imidazole or 1-methylimidazole. However, in other embodiments, triethylamine and N,N-diisopropylethylamine may be used as the base. Following silylation, the mixture is filtered by conventional means to remove spent organic salts and other dark solids.

In one embodiment, the rapamycin 31,42-bis-O-trimethylsilyl ether is extracted in heptane at room temperature and then separated from the dark insoluble impurities by filtration, using conventional means. Following filtration, the filtrate is mixed with charcoal. In one embodiment, Darco® KB charcoal is used. However, other charcoal may be selected by one of skill in the art, such as Nuchar® SA charcoal or Darco® G-60 charcoal. The charcoal contributes to the removal of color. Additionally, it prevents formation of emulsions during sodium bicarbonate washing.

The solution is then filtered and the filtrate is subjected to one or more water and basic washes. In one embodiment, the basic wash is sodium bicarbonate. In another embodiment, the filtrate is first washed with water, then with saturated sodium bicarbonate solution, and then again with water.

The organic layer is then removed and concentrated under reduced pressure at about 25° C. to about 30° C. to obtain a pale yellow foam. The foam is then dissolved in a suitable solvent and cooled to about 0° C. to about 5° C. In one embodiment the solvent is acetone. In other embodiments, the solvent is tetrahydrofuran, acetonitrile, or acetic acid. Other suitable solvents may be selected by one of ordinary skill in the art.

The silyl groups of the extracted rapamycin 31,42-bis-O-TMS are then removed, i.e., the rapamycin 31,42-bis-O-TMS is de-protected, using a suitable acid in order to generate rapamycin. In one embodiment, the acid used is sulfuric acid. In another embodiment, the sulfuric acid is 0.5 N sulfuric acid.

In one embodiment, the rapamycin produced according to the present invention has a purity greater than about 95% (by HPLC area %). In another embodiment, the rapamycin has a purity of greater than about 98%. In one embodiment, the rapamycin has a yellow index (also referred to herein as a yellow color index) of 1.0 or lower. In yet another embodiment, the rapamycin has a purity of greater than 95% and a yellow color index less than 1. In still another embodiment, the rapamycin has a purity of greater than 98% and a yellow color index less than 1.

Optionally, in order to increase the B:C isomeric ratio of the product, the pH of the reaction mixture is adjusted to a pH of about 5 to about 6. In one embodiment, aqueous sodium bicarbonate and acetic acid are added to an acetone solution of rapamycin. In one embodiment, the volume ratio of acetone and buffer is then adjusted via addition of sodium acetate-acetic acid buffer solution. In another embodiment, potassium acetate or zinc acetate is used. In another embodiment, the buffer solution has a pH from about 5 to about 5.5. Other buffer systems, acids, etc., to adjust the pH would be known to one of skill in the art and are contemplated by the process of the invention. Scheme 2 on the following page provides a representation of the change in isomer balance generated through this pH adjustment.

The purified rapamycin solution is stirred at room temperature (about 20° C. to about 25° C.) to yield precipitated product. In one embodiment, the reaction mixture is stirred for 60 hours. The product is then collected via conventional filtration means. The collected product is then washed. In one embodiment, the product is washed with a 1:1 (v/v) mixture of acetone and water. In another embodiment, the washing is performed twice. One of skill in the art would be aware of other schemes to wash the product, which are contemplated by the process of the invention.

In one embodiment, the washed product is dried under vacuum at approximately 35 to 40° C., although the drying conditions are not a limitation of the invention.

The purified rapamycin obtained by the processes of the invention is useful in pharmaceutical compositions. Thus, the rapamycin obtained can be formulated by any suitable method described in the art for rapamycin. In one embodiment, a composition contains the purified rapamycin obtained and a physiologically compatible carrier. As used herein the term carrier is intended to mean a physiologically compatible carrier. Suitable carriers for use in compositions of the invention are described below.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modi-

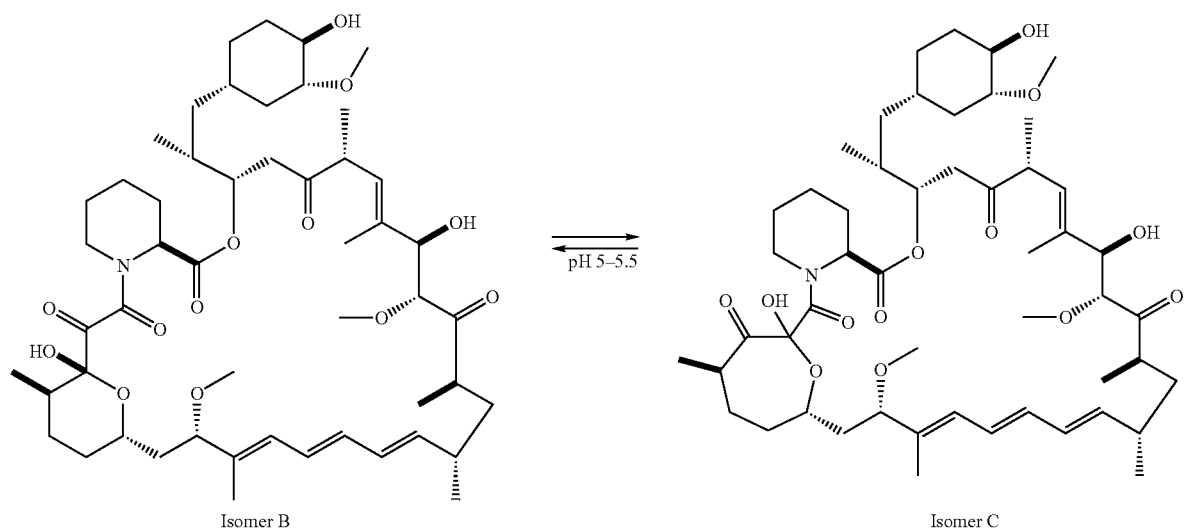

Scheme 2

Isomer B    Isomer C

In one embodiment, the isomeric B:C ratio obtained through buffering is greater than about 30:1. In another embodiment, the isomeric B:C ratio is greater than about 35:1.

fying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The parenteral formulations useful in this invention can be used to produce a dosage form that is suitable for administration by either direct injection or by addition to sterile infusion fluids for intravenous infusion.

Transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The present invention further provides packaging and kits containing the purified rapamycin produced according to the present invention and formulated for administration by a suitable delivery method. In one embodiment, the purified rapamycin is present in unit dosage form. A variety of suitable containers, including bottles, vials, blister packs, and the like are known to those of skill in the art. Such packaging and kits may further contain other components, including, e.g., instructions for use, syringes, applicators, and the like.

The following example is illustrative of the present invention, but is not a limitation thereof.

EXAMPLE

Purification of Rapamycin via Rapamycin 31,42-bis-O-trimethylsilyl Ether

A solution of crude rapamycin (20.0 g, 19.5 mmol, yellow index=24.23, purity=89% and B:C isomeric ratio=11:1) in 300 ml ethyl acetate was cooled to 0-5° C. Imidazole (6.0 g, 88.1 mmol) was added and the mixture stirred to form a solution. To this cold solution was added dropwise 8.73 g (80.4 mmol) of chlorotrimethylsilane over 30 min and stirred for a further 30 min at 0-5° C. to complete the formation of rapamycin 31,42-bis-O-trimethylsilyl ether. The reaction mixture was filtered and the filtrate concentrated under reduced pressure to a dark foam, which was stirred with 400 ml of heptane at room temperature for 20-30 minutes. The mixture was filtered to separate the insoluble material. The filtrate was stirred with 3.0 g of Darco® KB charcoal at room temperature for 20-30 minutes then filtered and the filtrate was further washed with water (160 ml), saturated sodium bicarbonate solution (80 ml) then with water (2×80 ml) to pH 6-7. The light yellow organic layer was concentrated under reduced pressure at 25-30° C. to obtain 24.0 g of product as a pale yellow foam.

The foam (24.0 g) was dissolved in 100 ml of acetone, stirred and cooled to 0-5° C. To this cold solution was added, dropwise, 20 ml of 0.5 N sulfuric acid over 10 minutes. The mixture was stirred at 0-5° C. until reaction completion. A solution of sodium bicarbonate (1.68 g/20 ml water) was added over 2-5 minutes. The pot temperature was allowed to rise to 10-15° C. Acetic acid (2 ml) was added and the mixture stirred for 15-20 minutes. To the reaction mixture was added, portionwise, 50 ml of sodium acetate buffer solution (pH 5-5.5) over 10 minutes and the mixture stirred at ambient temperature for 60 hours. The reaction mixture was filtered and washed with acetone-water (1:1; v/v) mixture (2×60 ml). The product was dried in vacuum oven at 35-40° C. to constant weight to obtain 15.58 g of product as a white solid. The proton NMR of the product was identical with an authentic sample.

The recovery yield was 87.6%, the purity of the product was 98.7%, the B:C isomeric ratio was 35:1, and the yellow index was 0.73.

All patents, publications, and other documents identified herein are incorporated by reference. One of skill in the art will recognize that minor modifications to the conditions and techniques described in the specific embodiments described herein can be varied without departing from the present invention. Such minor modifications and variants are within the scope of the invention as defined by the following claims.

The invention claimed is:

1. Rapamycin having a purity of greater than 98%, a yellow color index less than 1, and an isomeric B:C ratio greater than 30:1.

2. Rapamycin according to claim 1 having an isomeric B:C ratio greater than 35:1.

3. A composition comprising rapamycin according to claim 1 and a physiologically compatible carrier.

4. A process for purifying rapamycin, which comprises:
   (a) treating rapamycin with chlorotrimethylsilane in an inert solvent in the presence of a suitable base to provide rapamycin 31,42-bis-O-trimethylsilyl ether;
   (b) filtering the rapamycin 31,42-bis-O-trimethylsilyl ether;
   (c) extracting the rapamycin 31,42-bis-O-trimethylsilyl ether in heptane;
   (d) washing the extracted rapamycin 31,42-bis-O-trimethylsilyl ether; and
   (e) deprotecting the extracted rapamycin 31,42-bis-O-trimethylsilyl ether with acid to generate rapamycin having a purity of greater than 98%, a yellow color index less than 1, and an isomeric B:C ratio greater than 30:1.

5. The process according to claim 4, wherein step (d) comprises:
   (i) filtering the solution of step (c);
   (ii) mixing the filtrate with charcoal;
   (iii) washing the filtrate with water and sodium bicarbonate;
   (iv) concentrating the filtrate; and
   (v) dissolving the filtrate in a suitable solvent.

6. The process according to claim 5, wherein the suitable solvent is selected from the group consisting of acetone, tetrahydrofuran, acetonitrile and acetic acid.

7. The process according to claim 5, wherein the suitable solvent is acetone.

8. The process according to claim 4, further comprising:
   (f) adjusting the pH of the rapamycin solution to a pH of about 5 to about 6.

9. The process according to claim 8, wherein the rapamycin produced thereby has an isomeric B:C ratio of greater than 35:1.

10. The process according to claim 8, wherein the pH is adjusted with a buffer solution of sodium acetate, potassium acetate or zinc acetate.

11. The process according to claim 10, wherein the buffer solution is sodium acetate.

12. The process according to claim 8, further comprising the steps of:
   (g) precipitating the rapamycin;
   (h) collecting the rapamycin by filtration;
   (i) washing the rapamycin with a mixture of acetone and water; and
   (j) drying the rapamycin under vacuum.

13. The process according to claim 4, wherein the inert solvent in step (a) is ethyl acetate.

14. The process according to claim 4, wherein the suitable base in step (a) is imidazole.

15. The process according to claim 4, wherein the acid in step (e) is sulfuric acid.

16. A process for purifying rapamycin, which comprises:
   (a) treating rapamycin with chlorotrimethylsilane in an inert solvent comprising ethyl acetate in the presence of a base comprising an imidazole to provide rapamycin 31,42-bis-O-trimethylsilyl ether;
   (b) filtering the rapamycin 31,42-bis-O-trimethylsilyl ether;
   (c) extracting the rapamycin 31,42-bis-O-trimethylsilyl ether in heptane;
   (d) washing the extracted rapamycin 31,42-bis-O-trimethylsilyl ether; and
   (e) deprotecting the extracted rapamycin 31,42-bis-O-trimethylsilyl ether with acid comprising sulfuric acid to generate rapamycin having a purity of greater than 98%, a yellow color index less than 1, and an isomeric B:C ratio greater than 30:1.

17. The method according to claim 16, wherein the washing comprises one or more water and basic washes.

18. The method according to claim 16, further comprising concentrating the organic layer under reduced pressure to obtain a foam, following washing and prior to deprotecting the extracted rapamycin 31,42-bis-O-trimethylsilyl ether.

19. The method according to claim 18, wherein the concentrating is performed at about 25° C. to about 30° C.

20. The method according to claim 18, wherein the foam is dissolved in acetone and cooled to about 0° C. to about 5° C. prior to deprotecting.

* * * * *

UNITED STATES PATENT AND TRADEMARK OFFICE
CERTIFICATE OF CORRECTION

PATENT NO. : 7,384,953 B2
APPLICATION NO. : 11/359294
DATED : June 10, 2008
INVENTOR(S) : Shaw et al.

It is certified that error appears in the above-identified patent and that said Letters Patent is hereby corrected as shown below:

Column 1, Lines 47-66, replace

" 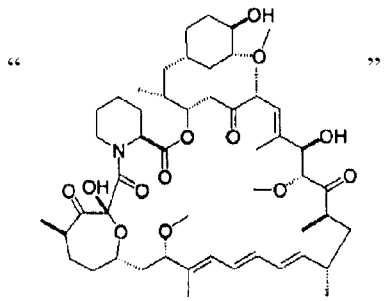 "  with  -- 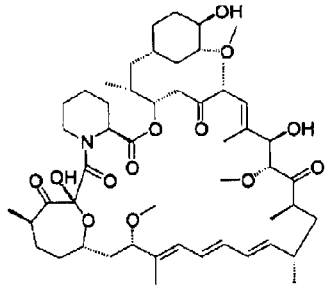 --

Isomer C                                 Isomer C

Signed and Sealed this

Seventh Day of October, 2008

JON W. DUDAS
*Director of the United States Patent and Trademark Office*